United States Patent [19]

Urbach et al.

[11] Patent Number: 5,550,255
[45] Date of Patent: Aug. 27, 1996

[54] CIS, ENDO-2-AZABICYCLOALKANE-3-CARBOXYLIC ACID DERIVATIVES

[75] Inventors: Hansjörg Urbach, Kronberg/Taunus; Rainer Henning, Hattersheim am Main; Winfried Hertzsch, Kelkheim, all of Germany

[73] Assignee: Hoechst Aktiengesellschaft, Frankfurt am Main, Germany

[21] Appl. No.: 202,478

[22] Filed: Feb. 28, 1994

Related U.S. Application Data

[62] Division of Ser. No. 882,376, May 6, 1992, abandoned, which is a continuation of Ser. No. 407,452, Sep. 14, 1989, abandoned, which is a division of Ser. No. 205,001, Jun. 2, 1988, Pat. No. 4,886,827, which is a continuation of Ser. No. 769,356, Aug. 26, 1985, abandoned.

[30] Foreign Application Priority Data

Aug. 28, 1984 [DE] Germany .......................... 34 31 541.1

[51] Int. Cl.⁶ ........................ C07D 209/52; A61K 31/405
[52] U.S. Cl. .................................................. 548/452
[58] Field of Search ........................................... 548/452

[56] References Cited

U.S. PATENT DOCUMENTS

| | | |
|---|---|---|
| 4,374,847 | 2/1983 | Gruenfeld . |
| 4,508,729 | 4/1985 | Vincent et al. . |
| 4,525,301 | 6/1985 | Henning et al. . |
| 4,558,064 | 12/1985 | Teetz et al. . |
| 4,558,065 | 12/1985 | Urbach et al. . |
| 4,562,202 | 12/1985 | Urbach et al. . |
| 4,587,258 | 5/1986 | Gold et al. . |
| 4,591,598 | 5/1986 | Urbach et al. . |
| 4,614,805 | 9/1986 | Urbach et al. . |
| 4,620,012 | 10/1986 | Henning et al. . |
| 4,659,838 | 4/1987 | Lerch . |
| 4,668,796 | 5/1987 | Geiger et al. . |
| 4,668,797 | 5/1987 | Urbach et al. . |
| 4,684,662 | 8/1987 | Henning et al. .......... 548/452 |
| 4,691,022 | 9/1987 | Henning et al. . |
| 4,714,708 | 12/1987 | Urbach et al. . |
| 4,727,160 | 2/1988 | Teetz et al. . |
| 4,808,573 | 2/1989 | Gold et al. . |
| 4,818,749 | 4/1989 | Gold et al. . |
| 4,822,894 | 4/1989 | Geiger et al. . |
| 4,831,157 | 5/1989 | Gold et al. . |
| 4,849,524 | 7/1989 | Henning et al. . |
| 4,868,307 | 9/1989 | Barton et al. . |
| 4,886,827 | 12/1989 | Urbach et al. . |
| 5,068,242 | 11/1991 | Nickel . |
| 5,525,301 | 6/1985 | Henning et al. . |

FOREIGN PATENT DOCUMENTS

| | | |
|---|---|---|
| 0018549 | of 0000 | European Pat. Off. . |
| 0012845 | of 0000 | European Pat. Off. . |
| 0049658 | of 0000 | European Pat. Off. . |
| 0012401 | of 0000 | European Pat. Off. . |
| 0090362 | of 0000 | European Pat. Off. . |
| 0046953 | of 0000 | European Pat. Off. . |
| 0037231A2 | of 0000 | European Pat. Off. . |
| 0050850A1 | of 0000 | European Pat. Off. . |
| 0079022 | of 0000 | European Pat. Off. . |
| 0050800A1 | of 0000 | European Pat. Off. . |
| 79022 | of 1983 | European Pat. Off. . |
| 0173199 | 8/1984 | European Pat. Off. . |
| 813422 | of 0000 | Finland . |
| 813283 | of 0000 | Finland . |
| 812859 | of 0000 | Finland . |
| 813034 | of 0000 | Finland . |
| 2491469 | of 0000 | France . |
| 3322530 | of 0000 | Germany . |
| 64085 | of 0000 | Israel . |
| 57-77672 | of 1982 | Japan . |
| 57-112359 | of 1982 | Japan . |
| 57-91974 | of 1982 | Japan . |
| 198535 | of 0000 | New Zealand . |
| 198702 | of 0000 | New Zealand . |
| 81/5988 | of 0000 | South Africa . |
| 832229 | of 0000 | South Africa . |
| 2086390 | of 0000 | United Kingdom . |
| 2095682 | of 0000 | United Kingdom . |

OTHER PUBLICATIONS

Leonard et al., J. Am. Chem. Soc., 77, 439 (1955).
Leonard et al., J. Am. Chem. Soc., 78, 3457 (1956).
Leonard et al., J. Am. Chem. Soc., 78, 3463 (1956).
Leonard et al., J. Am. Chem. Soc., 81, 5627 (1959).
Koelsch et al., J. Org. Chem., 26, 1104 (1961).
Griot et al., Helv. Chim. Acta, 42, 121 (1959).
Bonnet et al., J. Chem. Soc., 2087 (1959).
Battersby et al., J. Chem. Soc., 4333 (1958).
Rosenblatt et al., The Chemistry Of Functional Groups. Supplement F: The Chemistry of Amino, Nitroso and Nitro Compounds And Their Derivatives. Part II, S. Patai, ed., Wiley & Sons: New York 1982, pp. 1100–1104.

(List continued on next page.)

Primary Examiner—Nicholas Rizzo
Attorney, Agent, or Firm—Finnegan, Henderson, Farabow, Garrett & Dunner, L.L.P.

[57] ABSTRACT

The invention relates to compounds of the formula I

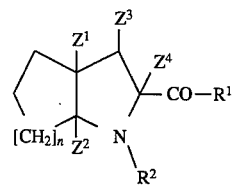

(I)

in which
n is 1, 2 or 3,
$Z^1$ and $Z^2$, and $Z^3$ and $Z^4$, in each case together represent a chemical bond or
$Z^1$, $Z^2$, $Z^3$ and $Z^4$ in each case represent hydrogen,
$Z^1$ and $Z^2$ being in the cis configuration relative to one another and the $COR^1$ group on C atom 3 being in the endo configuration relative to the bicyclic ring system,
$R^1$ denotes hydroxyl, alkoxy, aralkoxy, amino, alkylamino or dialkylamino and
$R^2$ denotes hydrogen, alkyl, aryl, aralkyl, cycloalkyl or alkylcycloalkyl,
processes for their preparation and their use.

14 Claims, No Drawings

OTHER PUBLICATIONS

L. W. Haynes, Enamines, A. G. Cook, ed., Marcel Decker, Inc.: 1969, pp. 68–79, 261–269, 413.
Fieser & Fieser, Reagents For Organic Synthesis, vol. 1, pp. 644–651 (1967).
Boehme et al., Iminium Salts in Organic Chemistry, Part I (E. C. Taylor, ed.), Wiley & Sons: New York, 1976, p. 143.
S. Dayagi et al., The Chemistry Of Functional Groups. The Chemistry Of The Carbon–Nitrogen Double Bond, S. Patai, ed., Wiley & Sons: New York, 1970, p. 119.
W. Greenlee et al., J. Med. Chem., 28, 434–442 (1985).
K. Ogawa et al., J. Chem. Soc., Perkin Trans. I, 3031–3035 (1982).
R. Bacon and D. Stewart, J. Chem. Soc. (C), 1384–1387 (1966).
R. Bacon et al., J. Chem. Soc. (C), 1388–1389 (1966).
Patchett et al., Nature, 288, 280–283 (1980).
Booth et al., Chemistry and Industry, 466–467 (1956).
Booth et al., J. Chem. Soc., Part I, 1050–1054 (1959).
Murakoshi et al., Chemical Abstracts, 61, 9465(e)(1964).
Cushman et al., Fed Proc., 38 (13), 2778–2782 (1979).
Houben–Weyl, Methoden der Organischen Chemie, 7(2b), 1403–1404 (1976).
Katritskaya, Dzh. Lagorskaya Khimia Geterosikl. Soedin., Moskow 1963, pp. 155–158.
Anderson, Jr. et al., J. Org. Chem., 43(1), 54–57 (1978).
Bertho et al., "Synthesen In Der 2–Azabicyclo[0.3.3]–octan–Reihe", Chemische Berichte, 92(7), 2218–2235 (1959).
Farkas et al., J. Org. Chem., 22, 1261–1263 (1957).
Taylor et al., J. Org. Chem., 38(16), 2817–2821 (1973).
Taylor et al., Heterocycles, 25, 343–345 (1987).
English language translation of Mitzlaff et al., Liebig's Ann. Chem., 1713–1733 (1978).
Chem. Berichte 86: 1524–1528 (1953).
Quarterly Reviews 25: 323–341 (1971).
Chem. Abst. 49/1955/3009c.
Nakanishi et al., Chem. Lett., (7), 869–872 (1981).
Nakanishi et al., Chemical Abstracts No. 95:150317j (1981).
Journal fur Praktische Chemie, 314 (1972) pp. 353–364.
Ziegenbein et al., Chem, Ber. (1960) pp. 2743–2749.

CIS, ENDO-2-AZABICYCLOALKANE-3-CARBOXYLIC ACID DERIVATIVES

This is a division of application Ser. No. 07/882,376 filed May 6, 1992, abandoned which is a continuation of application Ser. No. 07/407,452, filed Sep. 14, 1989, abandoned which is a divisional of application Ser. No. 07/205,001, filed Jun. 2, 1988, now U.S. Pat. No. 4,886,827 which is a continuation of application Ser. No. 06/769,356, filed Aug. 26, 1985, now abandoned.

The invention relates to compounds of the formula I

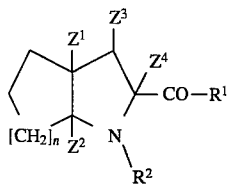

in which n is 1, 2 or 3 and a) $Z^1$ and $Z^2$, and $Z^3$ and $Z^4$, in each case together represent a chemical bond,
 $R^1$ denotes hydroxyl, $(C_1-C_6)$-alkoxy, $(C_6-C_{12})$-aryl-$(C_1-C_4)$-alkoxy, amino, $(C_1-C_6)$-alkylamino or di-$(C_1-C_6)$-alkylamino and
 $R^2$ denotes hydrogen, $(C_1-C_8)$-alkyl, $(C_6-C_{12})$-aryl, $(C_6-C_{12})$-aryl-$(C_1-C_4)$-alkyl, $(C_3-C_8)$-cycloalkyl or $(C_7-C_{12})$-alkylcycloalkyl, or b) $Z^1$, $Z^2$, $Z^3$ and $Z^4$ in each case represent hydrogen, $Z^1$ and $Z^2$ being in the cis configuration relative to one another and the $COR^1$ group on C atom 3 being in the endo configuration relative to the bicyclic ring system,
 $R^1$ denotes hydroxyl, $(C_1-C_6)$-alkoxy, $(C_6-C_{12})$-aryl-$(C_1-C_4)$-alkoxy, amino, $(C_1-C_6)$-alkylamino or di-$(C_1-C_6)$-alkylamino and
 $R^2$ denotes $(C_1-C_8)$-alkyl, $(C_6-C_{12})$-aryl, $(C_6-C_{12})$-aryl-$(C_1-C_4)$-alkyl, $(C_3-C_8)$-cycloalkyl or $(C_7-C_{12})$-alkylcycloalkyl, with the exception of the compounds of the formula I, known from J. prakt. chem. 314 [1972] 353, 354, in which $Z^1-Z^4$ are defined as under a), n=1, 2 or 3, $R^1$ denotes ethoxy and $R^2$ denotes methyl.

Alkyl (as such or as a constituent of other radicals) can be straight-chain or branched. Aryl is understood here, and in the following text, as meaning preferably phenyl, naphthyl or biphenylyl, especially phenyl.

European Patent Document A-79022 has disclosed compounds of the formula IV and its mirror image

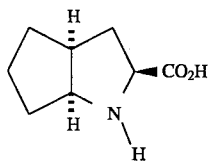

in which the hydrogens on the bridgehead C atoms are in the cis configuration relative to one another and the carboxyl group on C atom 3 is n the endo configuration relative to the bicyclic ring system, as well as a process for the preparation by reaction of an enamine of cyclopentanone with a compound of the formula V

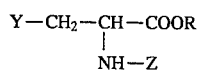

in which R denotes alkyl or aralkyl, Y denotes a nucleus-repelling group and Z denotes alkanoyl, aroyl or another protecting group conventionally used in peptide chemistry, cyclization of the resulting compounds of the formula VI

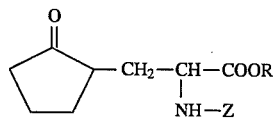

to give compounds of the formula VIIa or VIIb

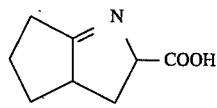

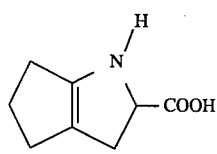

and subsequent hydrogenation of these compounds (see reaction scheme I).

Reaction scheme I (starting materials available commercially):

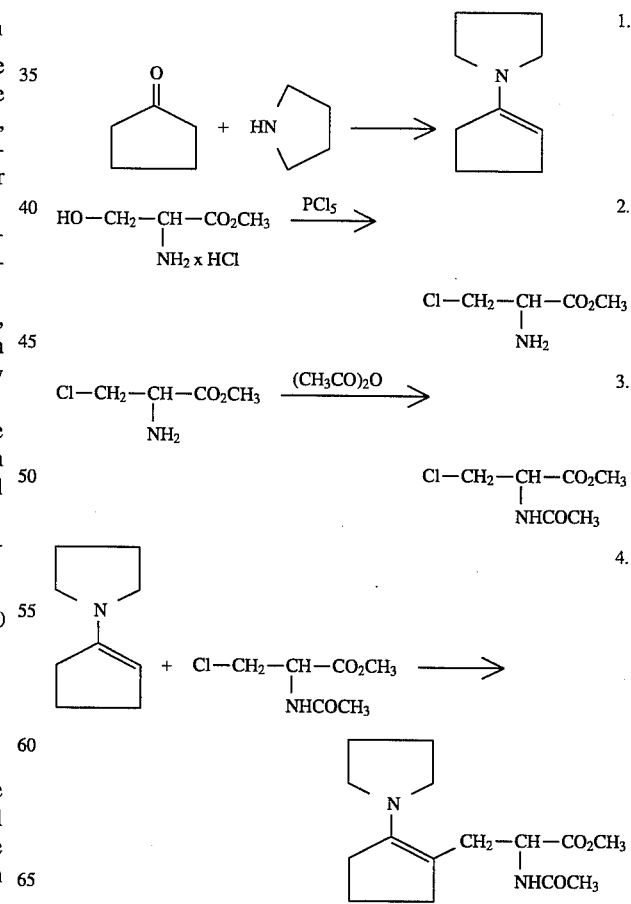

Reaction scheme I -continued

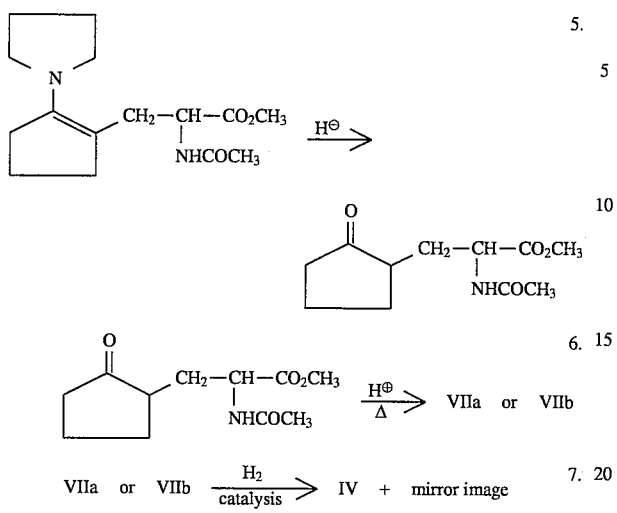

If commercially available starting materials are used (cyclopentanone and D,L-serine methyl ester hydrochloride), the compound of the formula IV+mirror image are obtained in a 7-step synthesis. As the compounds of the formula IV are intermediates in the preparation of highly active angiotensin-converting enzyme inhibitors, as disclosed in European Patent Document A-79022, it is of great interest to prepare compounds of the formula IV or related compounds in a particularly economic manner, i.e. using inexpensive starting materials, in the smallest possible number of reaction steps.

The compounds of the formula I according to the invention are easily obtainable intermediates in the preparation of highly active angiotensin-converting enzyme inhibitors.

Preferred compounds of the formula I are those in which $R^1$ denotes hydroxyl or $(C_1-C_6)$-alkoxy and $R^2$ denotes hydrogen or $(C_6-C_{12})$-aryl-$(C_1-C_6)$-alkyl, particular preference being given to those $(C_6-C_{12})$-aryl-$(C_1-C_6)$-alkyl radicals which can be removed by catalytic hydrogenation, such as, for example, benzyl, p-nitrobenzyl, p-methoxybenzyl, α-phenylethyl or benzhydryl.

Compounds of the formula I in which $Z^1$–$Z^4$ are defined as above under a) have 2 double bonds (see formula VIII).

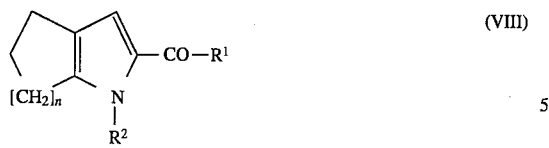

Compounds of the formula I in which $Z^1$–$Z^4$ are defined as above under b) possess two hydrogen atoms, on bridgehead atoms 1 and 5, which are in the cis configuration relative to one another and the CO—$R^1$ group is in the endo configuration relative to the bicyclic ring system. The carbon atom in the 3-position has the R configuration (formula IX) or S configuration (formula X). The present invention includes optically pure compounds of the formulae IX and X as well as a mixture thereof.

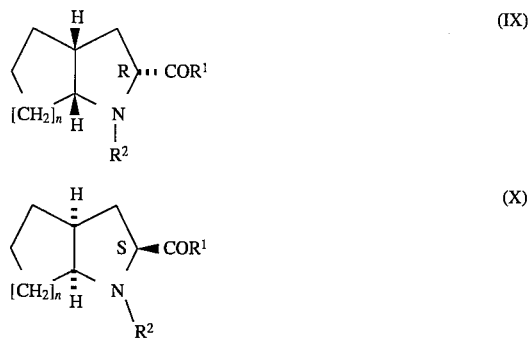

The S configuration in the 3-position is preferred.

Preference is also given to compounds of the formula I in which n=1, especially those compounds of the formula VIII in which $R^1$ denotes ethoxy and $R^2$ denotes benzyl.

The invention further relates to a process for the preparation of a compound of the formula I in which n is 1, 2 or 3, $Z^1, Z^2, Z^3$ and $Z^4$ in each case represent hydrogen, $Z^1$ and $Z^2$ being in the cis configuration relative to one another and the $COR^1$ group on C atom 3 being in the endo configuration relative to the bicyclic ring system, $R^1$ denotes hydroxyl, $(C_1-C_6)$-alkoxy, $(C_6-C_{12})$-aryl-$(C_1-C_4)$-alkoxy, amino, $(C_1-C_6)$-alkylamino or di-$(C_1-C_6)$-alkylamino and $R^2$ denotes hydrogen, $(C_1-C_8)$-alkyl, $(C_6-C_{12})$-aryl, $(C_6-C_{12})$-aryl-$(C_1-C_6)$-alkyl, $(C_6-C_8)$-cycloalkyl or $(C_7-C_{12})$-alkylcycloalkyl, wherein a compound of the formula I in which $Z^1$ and $Z^2$, and $Z^3$ and $Z^4$, in each case together represent a chemical bond and n, $R^1$ and $R^2$ are defined as above is catalytically hydrogenated, and also to a process for the preparation of a compound of the formula I in which $Z^1, Z^2, Z^3, Z^4, R^1$ and $R^2$ are defined as at the outset under a) and n has the above meanings, wherein a glycine derivative of the formula II

$$R^2-NH-CH_2-CO-R^1 \quad \text{(II)}$$

in which $R^1$ and $R^2$ are defined as above, is reacted with a compound of the formula III

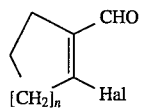

in which n is 1, 2 or 3 and Hal represents halogen, preferably chlorine.

Radicals $R^1 \neq$ hydroxyl can be cleaved to form $R^1$=hydroxyl, if appropriate with the aid of an acid or a base. Preferred acids are mineral acids such as $H_2SO_4$ or HCl. Preferred bases are alkali metal hydroxides such as NaOH or KOH.

It is preferred to prepare a compound of the formula VIII in which n=1, $R^1$ denotes ethoxy and $R^2$ denotes benzyl. By catalytic hydrogenation with cleavage of the benzyl group, this compound can then be converted to a compound of the formula IX or X in which n=1, $R^1$ denotes ethoxy and $R^2$ denotes hydrogen.

The processes according to the invention have made it possible to reduce the number of reaction steps to four, with good yields, using inexpensive, commercially available starting materials (for example cyclopentanone and N-benzylglycine ethyl ester).

A preferred embodiment is shown in reaction scheme II ($R^1$=OH, $R^2$=H, n=1, 2, 3).

Reaction scheme II:

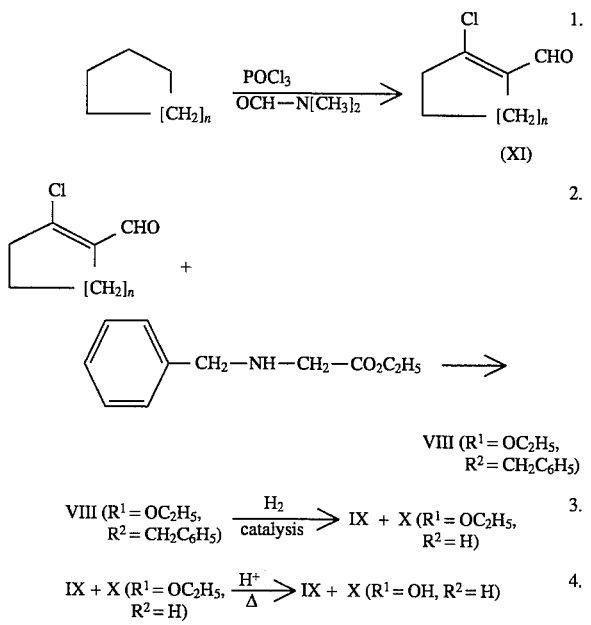

VIII ($R^1$ = OC$_2$H$_5$, $R^2$ = CH$_2$C$_6$H$_5$)

VIII ($R^1$ = OC$_2$H$_5$, $R^2$ = CH$_2$C$_6$H$_5$) $\xrightarrow[\text{catalysis}]{H_2}$ IX + X ($R^1$ = OC$_2$H$_5$, $R^2$ = H)   3.

IX + X ($R^1$ = OC$_2$H$_5$, $R^2$ = H) $\xrightarrow[\Delta]{H^+}$ IX + X ($R^1$ = OH, $R^2$ = H)   4.

If glycine derivatives of the formula (II) in which $R^1$ and $R^2$ have the meanings given above are used in the 2nd reaction step, compounds of the formula VIII are obtained which are catalytically hydrogenated to give compounds of the formula IX and its mirror image X.

In a preferred process according to the invention, the compounds of the formula XI in which n=1,2 or 3, known from the literature (Chem. Ber., 2743 (1960)), which are very readily obtainable in very good yield, are reacted with glycine derivatives of the formula II. The reaction is particularly preferably carried out with N-benzylglycine ethyl ester. The reaction can be carried out without a solvent in such a way that equivalent quantities of the compounds of the formulae II and XI are reacted in the presence of an organic base such as, for example, triethylene, diisopropylethylamine, dicyclohexylethylamine, N-ethylmorpholine etc., in a temperature range between 0° and 160° C., preferably between 20° C. and 120° C. The base can be used in an equimolar proportion, in excess or in a quantity less than the stoichiometric proportion. The organic base can also bee replaced by a corresponding excess of the compound II. The reaction described above is carried out without a solvent or in a polar or non-polar organic solvent, in a temperature range between 0° C. and the boiling point of the solvent. Toluene or benzene have proved particularly advantageous. At reflux temperature, the water of reaction formed can be entrained with these solvents. The water of reaction can also be removed with other water-binding agents such as, for example, MgSO$_4$, a molecular sieve, etc. The reaction mixture is extracted with a non-polar aprotic solvent such as, for example, hexane, petroleum ether etc., if appropriate after evaporation of the reaction solvents, the pyrrole derivative already being obtained in a relatively pure state. It can be used in this state of purity in the following reaction. If further purification is necessary, it can be filtered on silica gel or aluminum oxide with an organic solvent. The pyrrole derivative of the formula VIII is catalytically hydrogenated in an organic solvent, preferably in an alcohol such as, for example, ethanol or methanol, to give the compounds of the general formula IX and its mirror image X. The hydrogenation can be carried out at room temperature or an elevated temperature of up to 100° C., under normal conditions or under pressure. A temperature of between 20° and 60° C. and a pressure of between 1 and 100 bar are preferred. Suitable catalysts are Raney nickel or noble metal catalysts such as, for example, palladium, platinum or rhodium. Palladium-on-charcoal has proved particularly advantageous. The hydrogenation can be carried out in the presence of an inorganic or organic acid. The addition of sulfuric acid has been shown to be particularly advantageous. If compounds of the formula VIII in which $R^2$ is a radical which can be removed by hydrogenation, such as benzyl, are used in the hydrogenation reaction, compounds of the general formula I in which $R^2$=hydrogen are formed.

In the processes according to the invention, particular emphasis is to be placed on the selectivity of the hydrogenation reaction, which gives the cis,endo product diastereoselectively under the conditions indicated above.

The examples which follow are intended to illustrate the invention without thereby limiting it.

EXAMPLE 1

Ethyl 1-benzyl-1,4,5,6-tetrahydrocyclopenta[b]pyrrole-2-carboxylate 46.7 g (0.358 mol) of 2-chloro-1-formylcyclopent- 1-ene are dissolved in 400 ml of toluene. 138 g (0.716 mol) of N-benzylglycine ethyl ester are added. The mixture is refluxed for one hour, the ester of reaction being separated off via a water separator. After cooling, any precipitate formed is filtered off with suction and the toluene solution is washed with water, dried and concentrated. The residue is taken up in 300 ml of ethanol, 600 ml of 2N hydrochloric acid are added and the mixture is extracted 3x with petroleum ether. The petroleum ether phase is washed with 2×175 ml of ethanol/2N hydrochloric acid 1:2 and then with 100 ml of saturated NaHCO$_3$ solution, the organic phase is dried over MgSO$_4$, stirred with active charcoal and filtered with suction, and the filtrate is evaporated in vacuo.

Yield: 53.1 g of oil.

$^1$N-NMR (CDCl$_3$, 60 MHz): =1.26 (t; CH$_3$), 2.2–2.8 (s, 6H, 3CH$_2$), 4.18 (q; O-CH$_2$), 5.48 (s; N-CH$_2$), 6.78 (s; pyrrole-H), 6.9–7.5 (m; C$_6$H$_5$).

EXAMPLE 2

Ethyl 1-benzyl-1,4,5,6-tetrahydrocyclopenta[b]pyrrole-2-carboxylate 25 g (0.191 mol) of 2-chloro-1-formylcyclopent- 1-ene are added to 73.9 g (0.382 mol) of N-benzylglycine ethyl ester at room temperature and the mixture is then heated to 110° C. Working-up is carried out as indicated in Example 1.

EXAMPLE 3

Ethyl cis,endo-2-azabicyclo[3,3,0]octane-3-carboxylate 53.1 g of ethyl 1-benzyl-1,4,5,6-tetrahydrocyclopenta[b] pyrrole-2-carboxylate are dissolved in 450 ml of ethanol, and 5 g of Pd/C (10%) and 10.5 ml (19.3 g) of concentrated sulfuric acid are added to this solution. The mixture is then hydrogenated for 24 hours at 30° C. and under a hydrogen pressure of 100 bar. After the catalyst has been filtered off with suction, the solution is concentrated to half its volume in vacuo and adjusted to pH 7 with 2N sodium hydroxide solution. After concentration on a Rotavapor®, the residue is taken up in 2N hydrochloric acid and the aqueous solution is washed with methylene chloride. This solution is then rendered basic with $K_2CO_3$, saturated with NaCl and extracted with methylene chloride. After drying over $MgSO_4$ and treatment with active charcoal, the extract is concentrated in vacuo.

Yield: 28 g.

$^1$H-NMR (CDCl$_3$, 270 MHz): 1.25 (t; 3H), 1.32–1.70 (m; 7H), 1.32 (broad s; N$\underline{H}$), 2.27–2.39 (m; 1H), 2.50–2.66 (m; 1H), 3.59 (dd, $J_1$=6 Hz, $J_2$=10 Hz; $C_3$-H), 3.63 (m; $C_1$-H), 4.17 (q; OCH$_2$).

EXAMPLE 4

Ethyl 2-methyl-cis,endo-2-azabicyclo[3,3,0]octane-3-carboxylate 1.0 g of ethyl 1-methyl-1,4,5,6-tetrahydrocyclopenta[b]pyrrole-2-carboxylate (see Hauptmann et al., J. Prakt. Chem. 314, 353 (1972)) is dissolved in 50 ml of absolute alcohol and treated with 1.6 ml of concentrated sulfuric acid. 200 mg of rhodium-on-charcoal (5%) are added and the mixture is hydrogenated for 24 hours at 30° C. and under a hydrogen pressure of 10 bar. After the catalyst has been filtered off with suction, 8.3 g of saturated $K_2CO_3$ solution are added; the solution is extracted with methylene chloride and the extract is dried over $MgSO_4$ and concentrated.

Yield: 1.0 g (97% of theory) of an oil which is pure (cis,endo configuration) according to $^1$H-NMR at 270 MHz.

$^1$H-NMR (CDCl$_3$, 270 MHz): 1.26 (t; CH$_3$), 1.30–1.81 (m; 7H), 2.19–2.31 (m; $C_4$-H overlapping with s 2.30, N-CH$_3$), 2.44–2.60 (m; 1H), 2.78 (dd, $J_1$=6 Hz, $J_2$=8 Hz; $C_1$—H), 2.92 (dd, $J_1$=6 Hz, $J_2$=12 Hz; $C_3$-H), 4.17 (q; OCH$_2$).

What is claimed is:

1. A compound of the formula I

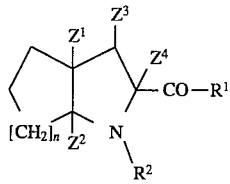

(I)

in which n is 1, 2 or 3 and a) $Z^1$ and $Z^2$, and $Z^3$ and $Z^4$, in each case together represent a chemical bond, $R^1$ denotes hydroxyl, ($C_1$–$C_6$)-alkoxy, ($C_6$–$C_{12}$)-aryl-($C_1$–$C_4$)-alkoxy, amino, ($C_1$–$C_6$)-alkylamino or di-($C_1$–$C_6$)-alkylamino and $R^2$ denotes ($C_6$–$C_{12}$)-aryl, ($C_6$–$C_{12}$)-aryl-($C_1$–$C_6$)-alkyl, ($C_3$–$C_8$)-cycloalkyl or ($C_7$–$C_{12}$)-alkylcycloalkyl, or b) $Z^1$, $Z^2$, $Z^3$ and $Z^4$ in each case represent hydrogen, $Z^1$ and $Z^2$ being in the cis configuration relative to one another and the COR$^1$ group on C atom 3 being in the endo configuration relative to the bicyclic ring system, $R^1$ denotes hydroxyl, ($C_1$–$C_6$)-alkoxy, ($C_6$–$C_{12}$)-aryl-($C_1$–$C_4$)-alkoxy, amino, ($C_1$–$C_6$)-alkylamino or di-($C_1$–$C_6$)-alkylamino and $R^2$ denotes ($C_6$–$C_{12}$)-aryl, ($C_6$–$C_{12}$)-aryl-($C_1$–$C_6$)-alkyl, ($C_3$–$C_8$)-cycloalkyl or ($C_7$–$C_{12}$)-alkylcycloalkyl, with the exception of the compounds of the formula I in which $Z^1$–$Z^4$ are defined as under a), n=1, 2 or 3, $R^1$ denotes ethyl and $R^2$ denotes methyl.

2. A compound of the formula VIII

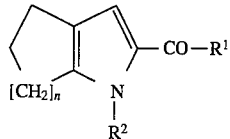

VIII in which n is 1, 2 or 3;

$R^1$ denotes hydroxyl, ($C_1$–$C_6$)-alkoxy, ($C_6$–$C_{12}$)-aryl-($C_1$–$C_4$)-alkoxy, amino, ($C_1$–$C_6$)-alkylamino or di-($C_1$–$C_6$)-alkylamino; and $R^2$ denotes hydrogen, ($C_1$–$C_8$)-alkyl, ($C_3$–$C_8$)-cycloalkyl or ($C_7$–$C_{12}$)-alkylcycloalkyl;

with the exception of compounds of the formula VIII (i) in which, simultaneously, $R^1$ denotes ethoxy and $R^2$ denotes methyl and (ii) in which, simultaneously, n=2, $R^1$ denotes ethoxy and $R^2$ denotes hydrogen.

3. A compound as claimed in claim 2, wherein $R^1$ denotes hydroxyl or ($C_1$–$C_6$)-alkoxy and $R^2$ denotes hydrogen.

4. A compound as claimed in claim 2, wherein n=1.

5. A compound of the formula IX or X

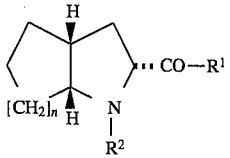

IX

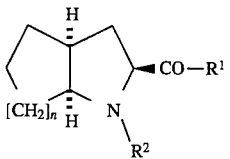

X in which n is 1, 2 or 3;

$R^1$ denotes hydroxyl, ($C_1$–$C_6$)-alkoxy, ($C_6$–$C_{12}$)-aryl-($C_1$–$C_4$)-alkoxy, amino, ($C_1$–$C_6$)-alkylamino or di-($C_1$–$C_6$)-alkylamino; and $R^2$ denotes ($C_6$–$C_{12}$)aryl, ($C_6$–$C_{12}$)-aryl-($C_1$–$C_6$)-alkyl, ($C_3$–$C_8$)-cycloalkyl or ($C_7$–$C_{12}$)-alkylcycloalkyl.

6. A compound as claimed in claim 5, wherein $R^1$ denotes hydroxyl or ($C_1$–$C_6$)-alkoxy and $R^2$ denotes ($C_6$–$C_{12}$)-aryl-($C_1$–$C_6$)-alkyl.

7. A compound as claimed in claim 5, wherein the C atom in the 3-position of the bicyclic ring system is in the S configuration.

8. A compound as claimed in claim 5, wherein n=1.

9. A compound as claimed in claim 5, wherein n=1, $R^1$ denotes ethoxy and $R^2$ denotes benzyl.

10. A compound as claimed in claim 2, with the exception of compounds of the formula I in which, simultaneously, n=1,2 or 3, $R^1$ denotes ethoxy and $R^2$ denotes hydrogen.

11. A compound as claimed in claim 10, wherein $R^1$ denotes hydroxyl or ($C_1$–$C_6$)-alkoxy and $R^2$ denotes hydrogen.

12. A compound as claimed in claim 10, wherein n=1.

13. A compound of the formula VIII

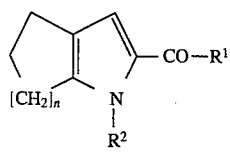

VIII in which n is 1, 2 or 3;

R¹ denotes hydroxyl, $(C_1-C_6)$-alkoxy, $(C_6-C_{12})$-aryl-$(C_1-C_4)$-alkoxy, amino, $(C_1-C_6)$-alkylamino or di-$(C_1-C_6)$-alkylamino; and R² denotes hydrogen, $(C_1-C_8)$-alkyl, $(C_6-C_{12})$-aryl, $(C_6-C_{12})$-aryl-$(C_1-C_6)$-alkyl, $(C_3-C_8)$-cycloalkyl or $(C_7-C_{12})$-alkylcycloalkyl;

with the exception of compounds of the formula VIII (i) in which, simultaneously, R¹ denotes ethoxy and R² denotes methyl and (ii) in which, simultaneously, n=2, R¹ denotes ethoxy and R² denotes hydrogen.

14. A compound of the formula IX or X

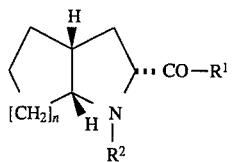

IX

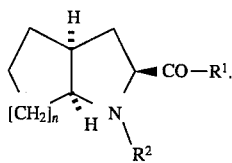

X in which n is 1, 2 or 3;

R¹ denotes hydroxyl, $(C_1-C_6)$-alkoxy, $(C_6-C_{12})$-aryl-$(C_1-C_4)$-alkoxy, amino, $(C_1-C_6)$-alkylamino or di-$(C_1-C_6)$-alkylamino; and R² denotes $(C_6-C_{12})$-aryl, $(C_6-C_{12})$-aryl-$(C_1-C_6)$-alkyl, $(C_3-C_8)$-cycloalkyl or $(C_7-C_{12})$-alkylcycloalkyl.

* * * * *